US00PP33751P2

(12) United States Plant Patent
Holtmaat

(10) Patent No.: US PP33,751 P2
(45) Date of Patent: Dec. 14, 2021

(54) ***ECHINACEA* PLANT NAMED 'PEARL495'**

(50) Latin Name: ***Echinacea* hybrid**
Varietal Denomination: PEARL495

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 17/185,923

(22) Filed: Feb. 25, 2021

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ... A01H 5/02; A01H 5/00; A01H 6/14; A01H 6/1448
See application file for complete search history.

*Primary Examiner* — June Hwu
(74) *Attorney, Agent, or Firm* — Penny J. Aguirre

(57) ABSTRACT

A new cultivar of *Echinacea* plant named 'PEARL495' that is characterized by its inflorescences with ray florets that are orange to orange-red in color and fused into a tubular shape, its very floriferous flowering habit, its compact, short plant habit, and its flowering season that commences early.

2 Drawing Sheets

Botanical classification: *Echinacea* hybrid.
Variety denomination: 'PEARL495'.

CROSS REFERENCE TO A RELATED APPLICATION

This application claims priority to European Community Plant Variety Office (CPVO) Plant Breeder's Rights Application No. 2020/2492 filed on Oct. 10, 2020, under 35 U.S.C. 119(f), the entire contents of which is incorporated by reference herein.

BACKGROUND OF THE INVENTION

The present invention relates to a new and distinct cultivar of *Echinacea* of hybrid origin and will be referred to hereafter by its cultivar name, 'PEARL495'. 'PEARL495' represents a new cultivar of coneflower, an herbaceous perennial grown for landscape use.

The new cultivar arose from an ongoing breeding program by the Inventor in Zuidwolde, The Netherlands with the objective of selecting new cultivars of *Echinacea* with strong plant habits and unique inflorescence colors. The new cultivar was selected as a unique seedling in a trial field by the Inventor in July of 2018. The trial field had been planted with seed collected from numerous cultivars and proprietary *Echinacea* seedlings from the Inventor's breeding program. The parentage of 'PEARL495' is therefore unknown.

Asexual propagation of the new cultivar was first accomplished by tissue culture using meristematic tissue in Heerhugowaard, The Netherlands in January of 2019 under the direction of the Inventor. Asexual propagation by tissue culture has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'PEARL495' as a unique cultivar of *Echinacea*.

1. 'PEARL495' exhibits inflorescences with ray florets that are orange to orange-red in color and fused into a tubular shape.
2. 'PEARL495' exhibits a very floriferous flowering habit.
3. 'PEARL495' exhibits a compact, short plant habit.
4. 'PEARL495' exhibits a flowering season that commences early.

The new cultivar can be most closely compared to the cultivars 'Echor273' (not patented) and 'Rainb299' (U.S. Plant Pat. No. 28,573). 'Echor273' and 'Rainb299' are both similar to 'PEARL495' in inflorescence shape. 'Echor273' differs from 'PEARL495' in having a taller height, a less compact plant habit, inflorescences that are larger in diameter, and ray florets that are un-fused with a lighter colored base. 'Rainb299' differs from 'PEARL495' in having inflorescences that are larger in diameter, ray florets that are unfused with a lighter colored base.

BRIEF DESCRIPTION OF THE DRAWINGS

The plants in the accompanying photographs depict the characteristics of a two-year-old plant of 'PEARL495' as field grown and placed in a 20-cm container in Zuidwolde, The Netherlands.

The photograph in FIG. 1 provides a side view of 'PEARL495' in bloom.

Figure 1:
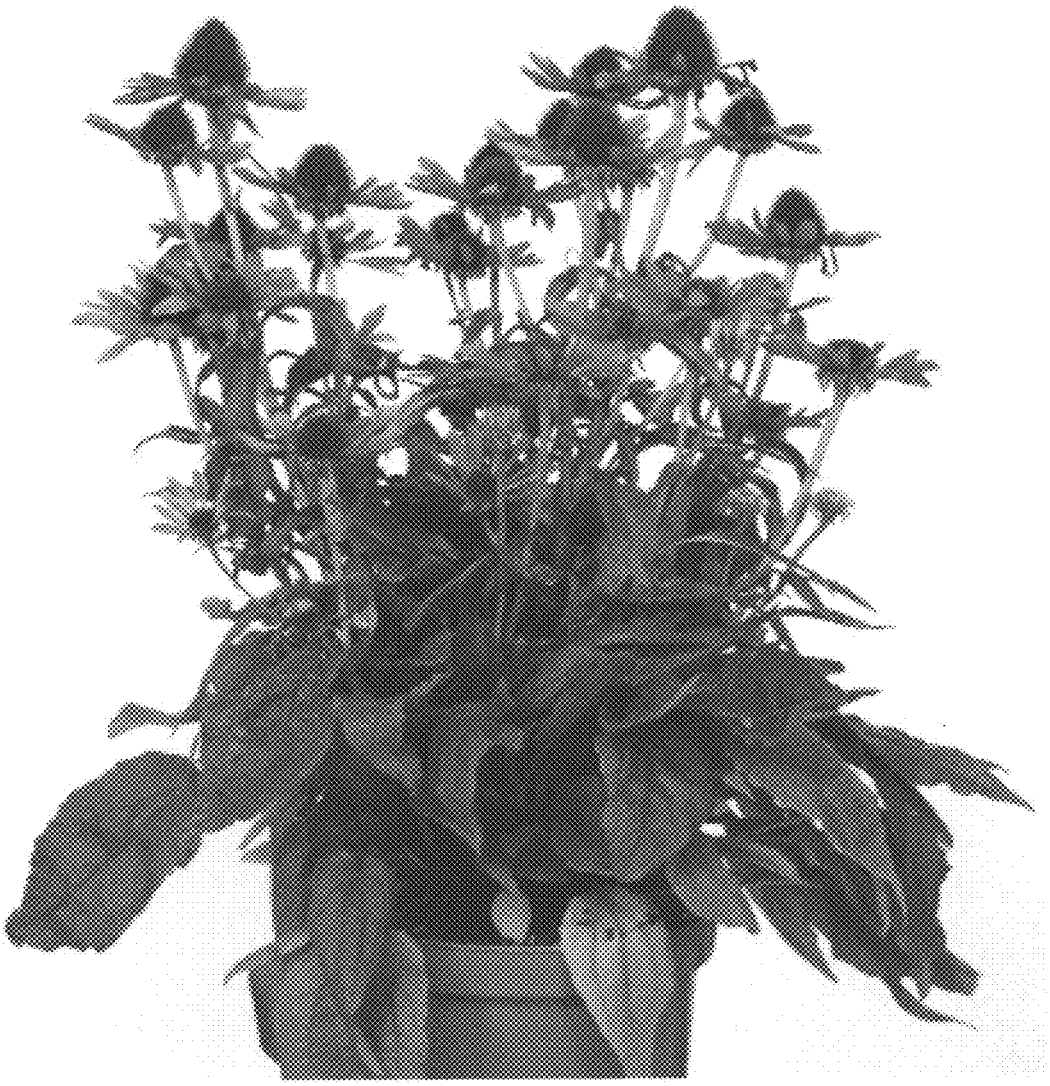
Figure 2:
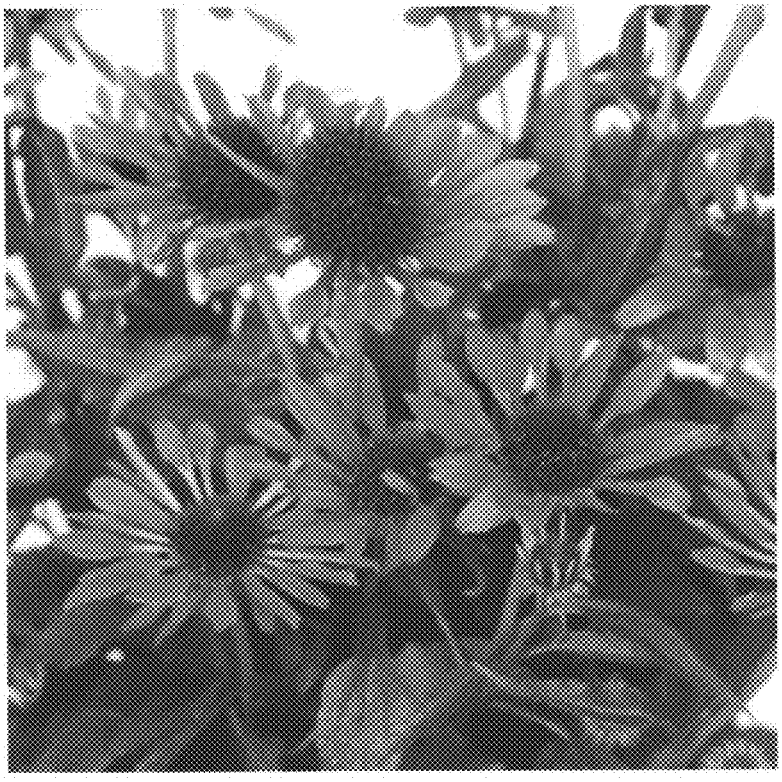

The photograph in FIG. 2 provides a close-up view of the inflorescences of 'PEARL495'.

Figure 3:
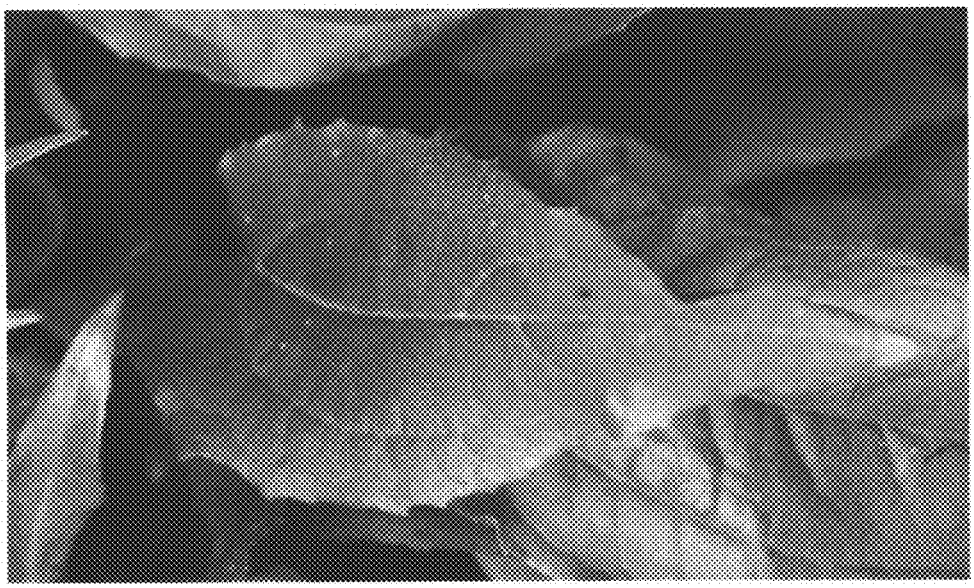

The photograph in FIG. 3 provides a close-up view of the foliage of 'PEARL495'.

The colors in the photograph may differ slightly from the color values cited in the detailed botanical description, which accurately describe the colors of the new *Echinacea*.

BOTANICAL DESCRIPTION OF THE PLANT

The plants in the accompanying photographs depict the characteristics of two-year-old plants of 'PEARL495' as field grown in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 10 weeks from summer and late summer (July until late September) in The Netherlands.

*Plant type*.—Herbaceous perennial.

*Plant shape*.—Broadly oblong to broadly ovate.

*Plant habit*.—Compact, upright.

*Height and spread*.—Average of 45 cm in height, 47 cm in width.

*Hardiness*.—At least in U.S.D.A. Zones 4 to 9.

*Diseases and pests*.—No resistance or susceptibility to pests or diseases has been observed.

*Root description*.—Fibrous.

*Propagation*.—Tissue culture.

*Root development*.—An average of 10 weeks for root development with a finished plant produced in about 3 months.

*Growth rate*.—Moderate.

Stem description:

*Shape*.—Rounded.

*Stem color*.—144B.

*Stem size*.—Average of 5.5 mm in diameter and an average of 21.9 cm in length.

*Stem surface*.—Rough to the touch, moderately covered with short strigose hairs; 0.4 mm in length, NN155D in color.

*Stem strength*.—Very strong.

*Stem aspect*.—Stems grow in an average angle of 20° from the base (0°=vertical).

*Branching*.—Main flowering stems grow from the base with a few lateral branches present, average of 16 primary branches, 2 branch per primary stem.

Foliage description:

*Leaf shape*.—Basal leaves; ovate, cauline leaves; narrow ovate.

*Leaf division*.—Simple.

*Leaf base*.—Narrow attenuate.

*Leaf apex*.—Narrowly acute.

*Leaf venation*.—Pinnate, upper surface; 148D, lower surface; 146D.

*Leaf margins*.—Entire, strongly undulate.

*Leaf attachment*.—Petiolate.

*Leaf arrangement*.—Alternate.

*Internode length*.—An average of 5.8 cm.

*Leaf size*.—Basal leaves; 13.7 cm in length, 6.3 cm in width, cauline leaves; 10 cm in length, 2.7 cm in width.

*Leaf color*.—Young upper surface; 137B, young lower surface; 146B, mature upper surface; NN137A, mature lower surface; 146B and 147B.

*Leaf surface*.—Both surfaces are slightly glossy, rough to the touch and moderately covered with very short strigose hairs; average length of 0.2 mm, too small to measure color.

*Petioles*.—On basal leaves an average of 13.8 cm in length and 2 mm in diameter, on cauline stem leaves V-shaped an average of 7.6 cm in length and 2.5 mm in diameter, surface is smooth and moderately covered with very short strigose hairs 0.2 mm in length and too small to measure color, color; upper surface; 144B, main veins 145B to 145C, changing to 187B at the end, lower surface 144A, changing to 187C at the end.

Inflorescence description:

*Type*.—Terminal capitulum, heterogamous with ray florets around the head margin and daisy-type disc florets in the center.

*Capitulum number*.—One terminal capitulum per lateral branch.

*Lastingness of inflorescence*.—About four weeks.

*Capitulum size*.—Matures to about 3.2 cm in height and 8.3 cm in diameter, disk is an average of 3.5 cm in diameter.

*Fragrance*.—Very faint, sweet, pleasant.

*Involucral bracts or phyllary*.—Average of 60 arranged in 3 rows, up to 1 cm in length and 2 mm in width, cuneate base, acute apex, narrow ovate in shape, curled downward into an average angle of −90°, entire margins, color; upper surface 138A, lower surface 138B, upper and lower surfaces smooth, matte, densely covered with very short hairs; average length of hairs 0.3 mm, too small to measure color.

*Buds*.—Flattened globular in shape, up to 1.8 cm in diameter and 2.2 cm in length, color; 143A, immature ray florets 173C, changing to 154C to 154D at the top.

*Peduncle*.—Strong, straight on top of main (flowering) stem, average of 8.5 cm in length, 4 mm in diameter, color; 144A, blotches of 144C, surface is moderately covered with very short hairs an average length of 0.3 mm in length, too small to measure color.

*Ray florets*.—Rotate, average of 19 (varying between 17 and 20), whorled, spatulate in shape, average of 3.9 cm in length and 9 mm in width, praemorse to emarginate apex, cuneate base, fused into tube, entire margin, held in a vertical angle, upper surface matte, velvety and glabrous, lower surface very slightly glossy, sparsely pubescent, color; upper surface when opening N25A, lower surface when opening 51B and 54A, upper surface when fully open N30C, changing to 34A at the base, lower surface when fully open 185C, veined 185B, upper surface fading to 172B and 173B, changing to 178B at the case, lower surface fading to 182C to 182D and 183C to 183D, tips tinged 146D.

*Disc florets*.—Numerous, average of 200, tubular, lower 87.5% fused, base fused into tube, arranged spirally on disc, average of 1 cm in length and 3 mm in width, entire margin, both surfaces glabrous, slightly glossy, color; upper surface when opening and fully open 183C, mid-section 151C, base 146D, lower surface when opening and fully open upper half 146B, outer margin 183C, mid-section 145D, base 144C.

*Receptacle*.—Narrow ovate in shape, average of 1.1 cm in height and 5 mm in diameter, 155B in color.

*Receptacle spines*.—An average of 200 per disc floret, acicular in shape, acute apex, attenuate base, 1.2 cm in length, 2 mm in diameter, glabrous and glossy surface, color: apex; 46A, mid-section; 42B, base; 144B.

Reproductive organs (present on disc florets only):

*Gynoecium*.—Pistil; 1, 6 mm in length, stigma; unequal, decurrent, 4 mm in length, N186C, style; 4.5 mm in length and 154D in color, ovary; 157D in color.

*Androecium*.—Stamens; 5, filaments; 3 mm in length, 157D in color, anther; linear in shape, 3 mm in length and N200A to N200B in color, pollen; moderate, 23A in color.

*Fruit/seed*.—No fruit or seed detected to date.

It is claimed:

1. A new and distinct cultivar of *Echinacea* plant named 'PEARL495' substantially as herein illustrated and described.

* * * * *